United States Patent [19]

Pellegata

[11] Patent Number: 5,182,300
[45] Date of Patent: Jan. 26, 1993

[54] FUROSEMIDE SALTS

[75] Inventor: Renato L. Pellegata, Milan, Italy

[73] Assignee: Roussel Uclaf, Paris, France

[21] Appl. No.: 602,008

[22] Filed: Oct. 23, 1990

[30] Foreign Application Priority Data

Oct. 24, 1989 [IT] Italy ................. 22118 A/89

[51] Int. Cl.$^5$ ...................... A61K 31/34; C07D 307/38
[52] U.S. Cl. ..................................... 514/471; 549/494
[58] Field of Search .......................... 549/494; 514/471

[56] References Cited

U.S. PATENT DOCUMENTS

| 4,663,348 | 5/1987 | Chafetz et al. | 549/494 |
| 4,698,361 | 10/1987 | DiSchiena | 549/494 |
| 4,908,382 | 3/1990 | Bianco | 514/471 |

FOREIGN PATENT DOCUMENTS

| 0043548 | 1/1982 | European Pat. Off. | 514/471 |
| 1943905 | 3/1971 | Fed. Rep. of Germany . | |
| 2189239 | 10/1987 | United Kingdom . | |

OTHER PUBLICATIONS

Neiss et al., "Antihypertensive Peptide Derivatives", CA 105 79371q (1986).

Primary Examiner—C. Warren Ivy
Assistant Examiner—A. A. Owens
Attorney, Agent, or Firm—Bierman and Muserlian

[57] ABSTRACT

Compounds of the formula

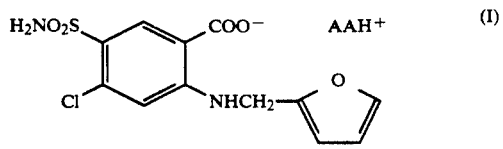

wherein AA is a basic amino acid in optically active or racemic form having better bio-availability and a method of treating asthma.

26 Claims, No Drawings

FUROSEMIDE SALTS

STATE OF THE ART

Furosemide or 4-chloro-N-furyl-5-sulfamoyl-anthranylic acid is a compound often used in medical practice as a diuretic, anti-hypertensive and anti-hypercalcemic agent. It has recently been discovered that furosemide when administered by aerosol to atopic asthmatic patients can also prevent bronchospasms induced by physical exercises, ultrasonic fogs and immunological stimulations. In the course of these studies, patients inhaled for 15 to 20 minutes an aerosol obtained by nebulization of a aqueous solution of 10 mg/ml of the sodium salt of furosemide, a commercially available formulation for parenteral administration and this formulation has a concentration close to saturation point.

This type of administration is long, complicated and, due to this fact, such a use of the pharmaceutical product in current therapeutic practice is almost impossible. In British Patent No. 2,189,239, furosemide salts with quaternary ammonium bases which are far more soluble and more bio-available than the corresponding sodium salt are described, but these salts are not suitable for administration by aerosol because quaternary ammonium bases and their salts very often cause a paroxysmal broncho-constriction in the patient.

OBJECTS OF THE INVENTION

It is an object of the invention to provide novel salts of furosemide and a process for their preparation.

It is another object of the invention to provide improved compositions and method for the treatment of warm-blooded animals suffering from asthma.

These and other objects and advantages of the invention will become obvious from the following detailed description.

THE INVENTION

The novel salts of the invention are compounds of the formula

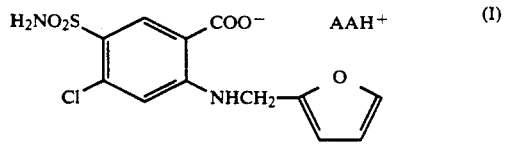

wherein AA is a basic amino acid in optically active or racemic form.

The basic amino acids of the invention are preferably amino acids of natural origin such as ornithine, lysine and arginine.

The salts of the invention are more stable from the physical and chemical point of view, offer a better bio-availability of furosemide and permit the preparation of spray formulations with which one can administer by a small jet quantities of furosemide equivalent to those that can be administered by aerosol using an aqueous solution of sodium salt.

Furosemide salts of the present invention are much more soluble in water than furosemide itself or its sodium salt. For example, the furosemide salt with L-lysine has a solubility in water of approximately 560 mg/ml, which corresponds to a furosemide concentration of approximately 400 mg/ml, and a solubility in a physiological solution of approximately 490 mg/ml, which corresponds to a furosemide concentration of approximately 310 mg/ml.

The preferred compounds of formula I are those in which the basic amino acid is L-lysine or DL-lysine.

The novel process of the invention for the preparation of the salts of formula I comprises reacting furosemide with a basic amino acid in a solvent or mixture of solvents at 0° C. to reflux of the solvent(s). The solvent is preferably at least one of the group consisting of water, methanol and/or ethanol. The salt may be recovered by precipitation from the reaction mixture or any other known procedure and can be purified, if desired, by crystallization from a solvent(s).

The novel compositions of the invention for the treatment of asthma comprise an asthma treating amount of at least one salt of formula I and an inert pharmaceutical carrier. The compositions may be in the form of tablets, dragees, capsules, granules, solutions, sprays, aerosols and injectable compositions.

Examples of excipients include talc, lactose, starch, magnesium stearate, aqueous and non-aqueous vehicles, glycols, wetting and dispersing agents and preservatives.

The compositions are useful for treatment of patients with high blood pressure and do not present the risk of causing a paroxysmal broncho-constriction reaction when administered in aerosol form in contrast to the quaternary ammonium salts.

As the salts of the invention are extremely soluble in water and as the bio-availability of a medicament is proportional to its speed of solubilization in this medium, these salts can be used for the preparation of pharmaceutical compositions in solid form in which the furosemide has a far greater solubility than the present commercially available solid pharmaceutical preparations. Furthermore, because of their stability characteristics, the salts can be used both for the preparation of pharmaceutical compositions intended for oral administration of the medicament in solid or liquid form and for the preparation of pharmaceutical compositions intended for parenteral route or for inhaling.

The following table contains information on the stability of the furosemide salt of L-lysine in aqueous solution.

TABLE

| Sol. No. | Preservation temp. | Solvent | Conc. mg/ml | pH(1) | Titer in furosemide(2) after | | | |
|---|---|---|---|---|---|---|---|---|
| | | | | | 10 d | 26 d | 37 d | 7 m | 12 m |
| 1 | 25° C. | water | 97.2 | 7.00 | — | 97.7 | 96.8 | | |
| 2 | 25° C. | physiol. sol. | 184.4 | 7.09 | — | 99.6 | 98.7 | | |
| 3 | 25° C. | water | 275.3 | 7.32 | — | 99.6 | 98.2 | | |
| 4 | 60° C. | water | 125.0 | 7.06 | 99.3 | | | | |
| 5 | 25° C.(3) | water | 125.0 | 7.06 | 100.0 | | | | |
| 6 | 25° C. | water | 90.4 | 6.95 | 99.4 | — | 98.9 | | |

TABLE-continued

| Sol. No. | Preservation temp. | Solvent | Conc. mg/ml | pH(1) | Titer in furosemide(2) after | | | | |
|---|---|---|---|---|---|---|---|---|---|
| | | | | | 10 d | 26 d | 37 d | 7 m | 12 m |
| 7 | 4° C. | water(4) | 72.1 | 7.06 | | | | 99.9 | 99.1 |

NOTES:
(1) Initial measurement of the pH.
(2) Expressed as percentage relative to the initial titer of furosemide.
(3) Preserved away from the light.
(4) Containing 4% by weight of mannitol.

In particular, as far as the inhalation route is concerned, the furosemide salts of the invention permit the preparation of spray formulations that can deliver, in a few small jets (2 to 4), the quantity of therapeutically active furosemide, thereby avoiding the long periods of time (15 to 20 minutes) that was necessary in the prior art and the use of an atomizer.

A preferable pharmaceutical composition is in the form of a spray containing a compound of formula I and a propulsive gas such as nitrogen, air or another inert gas.

Moreover, it is known that the administration of a medicament by aerosol can cause a paroxysmal broncho-constriction that appears to be due to the composition of the solution in aerosol form. In particular, this should not be hypotonic nor contain stabilizing agents such as EDTA, nor preservatives such as metabisulfite or quaternary ammonium salts like benzalkonium chloride. Now the furosemide salts of the invention permit the easy preparation of sterile isotonic or hypertonic solutions, and as the furosemide salts are with a natural basic amino acid, the administration by aerosol causes no paroxymal broncho-constriction, as is theoretic all possible with the compounds described in British Patent No. 2,189,239 where furosemide is salified with a quaternary ammonium base and therefore has the structure of preservatives to which is imputed this harmful collateral effect.

The novel method of the invention for treating asthma in warm blooded animals, including humans, comprises administering to warm-blooded animals an amount of at least one compound of formula I in an amount sufficient to treat asthma. The compounds may be administered orally, rectally, parenterally or nasally and the usual daily dose is 0.266 to 2.666 mg/kg depending on the condition treated, the method of administration and the specific salt administered.

In the following examples there are described several preferred embodiments to illustrate the invention. However, it is to be understood that the invention is not intended to be limited to the specific embodiments.

EXAMPLE 1

L-lysine salt of furosemide 200 ml of water, 150 g (0.45 mol) of furosemide and 118 ml (0.45 mol) of an aqueous solution with 50% w/w of L-lysine were mixed together and after stirring for about 30 minutes, 1 liter of 95% ethanol was added to obtain a clear solution. The solution was cooled to 8° to 10° C. and, another 1 liter of 95% ethanol was added with stirring. During this addition, a product started to precipitate. After stirring for 30 minutes and filtering under reduced pressure, the product was washed with a small amount of alcohol, then dried in an oven under reduced pressure at 40° C. to obtain 210 g (97% of the calculated amount) of the desired crystallized white product melting at 214° to 216° C. (decomp.) and having a specific rotation of $[\alpha]_D = +4.5°$ (c=2% in water).

| | I.R. (Nujol): | |
|---|---|---|
| Length of wave | Intensity | Allocation |
| 3380 | weak | Φ NH |
| 3300-2000 | widened | Φ $NH_3+$ |
| 1600, 1500, 1500 | strong | $NH_3+$, phenyl nucleus, Φ |
| | | C = 0 (group - $COO^-$) |
| 1410 | average | characteristic band |
| 1330, 1268 | strong | characteristic bands |
| 1160 | strong | Φ $SO_2$ |
| 975, 940, 840, 750 | average | characteristic bands |

| | NMR (DMSO): | | |
|---|---|---|---|
| N° protons | type | Multiplicity | Δ ppm |
| 1 | aromatic | singlet | 8.44 |
| 1 | " | doublet (j=3Hz) | 7.55 |
| 1 | " | singlet | 6.76 |
| 2 | " | absorp. complex | 6.35 (center) |
| 2 | $CH_2$—NH—CH | doublet* (j=3Hz) | 4.41 |
| 1 | CH—N | absorp. complex | 3.38 |
| 2 | CH—$CH_2$—N | absorp. complex | 3.0–2.55 |
| 6 | $CH_2$—$CH_2$—$CH_2$—CH | absorp. complex | 2.05–1.15 |

EXAMPLE 2

DL-lysine salt of furosemide

Using the procedure of Example 1, DL-lysine instead of L-lysine was reacted to obtain the corresponding furosemide salt in a yield of 98% melting at 228° to 230° C. (decomp.)

| | I.R. (Nujol): | |
|---|---|---|
| Length of wave | Intensity | Allocation |
| 3380 | weak | Φ NH |
| 3300-2000 | widened | $NH_3+$ |
| 1600, 1550, 1500 | strong | $NH_3+$, phenyl nucleus, Φ |
| | | C = 0 (group —$COO^-$) |
| 1410, 1330, 1268 | strong | characteristic band |
| 1160 | strong | Φ $SO_2$ |
| 975,940,840,750,685 | average | characteristic bands |

EXAMPLE 3

L-ornithine salt of furosemide

Using the procedure of Example 1, L-ornithine instead of L-lysine was reacted to obtain the corresponding furosemide salt in a yield of 92% melting at 202° to 203° C. (decomp.) and having a specific rotation of $[\alpha]_D = +4.3$ (c=1% in water).

EXAMPLE 4

DL-ornithine salt of furosemide

Using the procedure of Example 1, DL-ornithine instead of L-lysine was reacted to obtain the corresponding furosemide salt in a yield of 94% and melting at 188° to 189° C. (decomp.)

EXAMPLE 5

L-arginine salt of furosemide

Using the procedure of Example 1, L-arginine instead of L-lysine was reacted to obtain the corresponding furosemide salt in a yield of 82% and melting at 180° to 183° C. (decomp.) and having a specific rotation of $[\alpha]_D = +5.5$ (c=1% in water - ethanol mixture 4/1).

EXAMPLE 6

DL-arginine salt of furosemide

Using the procedure of Example 1, DL-arginine instead of L-lysine was reacted to obtain the corresponding furosemide salt in a yield of 84% and melting at 186° to 190° C. (decomp.).

EXAMPLE 7

L-lysine salt of furosemide

A) Composition:

One liter of solution contained 72.1 q of furosemide, lysine salt (corresponding to 50 g of furosemide), 40 mg of mannitol and sufficient water for 1 liter.

B) Preparation process:

Mannitol, then L-lysine furosemide salt were dissolved in two thirds of the quantity of p.p.i. water and then the remaining third of the p.p.i water was added [the pH of the resultant solution varied between 6.9 and 7.1]. The solution was filtered on a sterilizing membrane (0.22μm), then spread out in a sterile medium in 5 ml depyrogenated ampoules under excess pressure of very pure nitrogen. A small jet of the above-mentioned formulation delivered approximately 0.1 ml of solution corresponding to 7.22 mg of the furosemide salt of L-lysine, that is 5 mg of furosemide.

EXAMPLE 8

Dry form of L-lysine salt of furosemide intended for inhalation

A) Composition:

One kilogram of the mixture contained 361 g of the lysine salt of furosemide (corresponding to 250 g of furosemide and 639 g of mannitol.

B) Preparation process:

The two compounds were intimately mixed and then micronized to obtain a particle size of between 5 and 10 microns. The powder was then distributed in capsules of 40 mg (corresponding to 14.44 mg of the furosemide salt of L-lysine or 10 mg of furosemide). The content of the capsules could be administered with a powder inhaler currently used in medical practice.

Various modifications of the compounds and method of the invention may be made without departing from the spirit or scope thereof and it is to be understood that the invention is intended to be limited only as defined in the appended claims.

What I claim is:

1. A compound of the formula

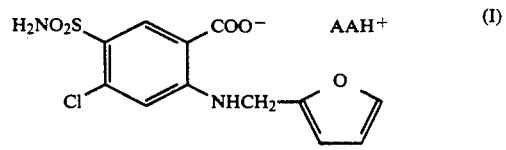

wherein AA is a basic amino acid in optically active or racemic form.

2. The compound of claim 1 wherein AA is selected from the group consisting of lysine, arginine and ornithine.

3. The compound of claim 1 wherein AA is L-lysine.

4. The compound of claim 1 wherein AA is DL-lysine.

5. The compound of claim 1 wherein AA is L-arginine.

6. The compound of claim 1 wherein AA is DL-arginine.

7. The compound of claim 1 wherein AA is DL-ornithine.

8. The compound of claim 1 wherein AA is L-ornithine.

9. An asthma treating composition comprising an asthma treating amount of at least one compound of claim 1 and an inert pharmaceuticl carrier.

10. The composition of claim 9 wherein AA is selected from the group consisting of lysine, arginine and ornithine.

11. The composition of claim 9 wherein AA is L-lysine.

12. The composition of claim 9 wherein AA is DL-lysine.

13. The composition of claim 9 wherein AA is L-arginine.

14. The composition of claim 9 wherein AA is DL-arginine.

15. The composition of claim 9 wherein AA is DL-ornithine.

16. The composition of claim 9 wherein AA is L-ornithine.

17. A method of treating asthma in warm-blooded animals comprising administering to warm-blooded animals an asthma treating effective amount of at least one compound of claim 1.

18. The method of claim 17 wherein AA is selected from the group consisting of lysine, arginine and ornithine.

19. The method of claim 17 wherein AA is L-lysine.

20. The method of claim 17 wherein AA is DL-lysine.

21. The method of claim 17 wherein AA is L-arginine.

22. The method of claim 17 wherein AA is DL-arginine.

23. The method of claim 17 wherein AA is DL-ornithine.

24. The method of claim 17 wherein AA is L-ornithine.

25. The method of claim 17 wherein the compound of claim 1 is administered in the form of a liquid spray.

26. The method of claim 17 wherein the compound of claim 1 is administered in the form of a dry powder.

* * * * *